United States Patent [19]

Sulc et al.

[11] Patent Number: 4,955,903
[45] Date of Patent: Sep. 11, 1990

[54] SOFT INTRACAMERAL LENS

[75] Inventors: Jiri Sulc; Zuzana Krcova; Karel Smetana; Sarka Pitrova, all of Prague, Czechoslovakia

[73] Assignee: Ceskoslovenska Akademie Ved, Prague, ; CSX

[21] Appl. No.: 379,575

[22] Filed: Jul. 12, 1989

Related U.S. Application Data

[62] Division of Ser. No. 076 127, Jul. 21, 1987.

[30] Foreign Application Priority Data

Jul. 22, 1986 [CS] Czechoslovakia ............ 5559-86

[51] Int. Cl.$^5$ .............................................. A61F 2/16
[52] U.S. Cl. .................................................... 623/6
[58] Field of Search ........................................... 623/6

[56] References Cited

U.S. PATENT DOCUMENTS 4,424,597 1/1984 Schlegel .................................. 623/6
4,846,832 7/1989 Wichterle .............................. 623/6

Primary Examiner—Alan W. Cannon
Attorney, Agent, or Firm—Leydig, Voit & Mayer

[57] ABSTRACT

The invention pertains to a soft intracameral lens intended for location in the posterior chamber of the eye.

The soft intracameral hydrogel lens has a front supporting and centering convex part intended for leaning against the iris having a rotational symmetrical shape of a sphere, paraboloid, or hyperboloid and passing into the broadest circumference by a surface, the shape of this surface being equal to or approaching the shape of the lateral area of a cone, while the hinder, or rear, supporting part of the lens has a spherical, planar, or moderately convex or concave-curved shape and a large surface area for leaning against a hinder capsula or a membrane of the vitreous body. The hinder supporting part is broadened and forms on its edge a retaining ring which reaches over the front part by as much as 1.5 mm, whereas the central thickness of the lens ranges between 1 to 3.5 mm. The surface of the soft intracameral lens may be formed, at least in part, from a soft hydrogel containing at least 70% water at 20°C. in the state of equilibrium swelling. The lens may have a spherical shape and be provided on the circumference with a supporting collar manufactured from a soft hydrogel. The lens may also contain inside, in its optical axis, an inner part, e.g., a Fresnel lens, having a higher refractive index of light than the material which surrounds the inner part of the lens.

1 Claim, 1 Drawing Sheet

SOFT INTRACAMERAL LENS

This is a division of application Ser. No. 076,127 filed July 21, 1987.

This invention pertains to soft intracameral lenses.

Common optical defects of the eye are usually corrected with either additional lenses placed in front of the eye (spectacles, monocles), on the eye surface (contact lenses), or with lenses replacing the original lens of the eye. These substitute lenses have, up to the present time, taken the form of very thick converging spectacle lenses. However, more recent developments now point to the placement of intracameral lenses directly into that area of the eye from which the natural lens has been removed (e.g. during cataract surgery).

Provided the original capsule (capsula lentis) is retained after this type of operation, even a hard intracameral lens may be placed into the eye. However, the disadvantage of this type of lens is that it possesses a higher refractive index due to its production from organic glass and thus it has a smaller dimension than the original natural lens. In addition, this lens also has a higher specific mass This last property makes it necessary to locate the substitute lens precisely in the optical axis of the eye, thus requiring additional fixating means. This requirement makes location of the lens in the correct position very difficult.

Therefore, there exists a need for an intracameral lens produced from a soft elastic material which would enable one to easily introduce the lens into the eye, the lens being in either a deformed or dry state, and which also has a specific mass approaching the specific mass of the natural lens.

In searching for such a lens, experiments were carried out with hydrogels, which up to the present time, proved suitable for soft contact lenses. More specifically, a lightly crosslinked poly(2-hydroxyethyl methacrylate) (polyHEMA) was investigated. However, it turned out that this material is not suitable for the production of intracameral lenses because minute calcifications are created on the surface of the lens such that the lens loses its original transparency. From this point of view, an intracameral lens manufactured using highly swelling gels proved to be superior e.g., gels having a swelling capacity in water amounting to 55-70% at 20° C. Despite this advance, the problem of correct centering of the lens and keeping it permanently located in the eye still remained unsolved. In addition, the high water content of highly swelling gels lowers the refractive index of the lens, this requiring the lens to have a considerable increase in thickness.

Intracameral lenses used at the present time are produced in a broad range of shapes and are located in various parts of eye, e.g., in the anterior chamber, pupil, and, most frequently, in the posterior chamber. The major part of these lenses is manufactured from a hard organic glass—poly(methyl methacrylate). Recently, there have been reports of soft lenses being produced from silicon rubber and from hydrogels.

All types of these lenses consist of two basic parts, the optical part and the supporting part. The optical part is formed by a converging lens having a value of 15-20 Dpt. The supporting part acts to center the lens and stabilize its position.

The supporting system, if made from various materials such as poly(methyl methacrylate), polypropylene or polyester, always wounds those parts of the eye that the lens leans against. Since most materials have a considerable specific mass and the surface of support action is very small, undesirable reactions to foreign bodies often occur at the point of contact and cause various complications after introduction of the lens into the eye.

Moreover, the hard intracameral lenses have a disadvantage in that they require a relatively large incision for introduction into the eye because they cannot be elastically deformed. Another disadvantage is their impermeability to gases, liquids, and ions.

The present invention solves the aforementioned problems by the design of a lens which utilizes the specific properties of soft types of hydrogels having a high water content and a low Young modulus and combining these with shape adaptability, thus producing an intracameral lens having the optical properties of a natural lens. The soft intracameral lens of the present invention is intended for location in the posterior chamber of eye. Upon insertion, the lens reaches with its front supporting and centering convex part up to the pupil in which it is spontaneously centered, while the surface area of this front part 6 continuously passes into a surface equal to or approaching the shape of lateral area of a cone, with the hinder, or rear, supporting part of the lens leaning against the hinder capsula or the membrane of the vitreous body. The hinder part is broadened and forms a retaining (safety) ring exceeding the front centering and supporting part by as much as 1.5 mm. This retaining ring prevents the lens from sliding out into the anterior chamber of the eye. The central thickness of the lens ranges advantageously from 1 mm to 3.5 mm. The shape and size of the lens acts to cause its automatic location in the eye axis.

In order to prevent any wounding of the eye tissues, it is very important that the lens surface be soft. Therefore, the lens according to the present invention may be either completely homogeneous in that it is manufactured using a single kind of material having a single refractive index value, or from two different materials, specifically, from a core having a higher refractive index and a casing having a lower refractive index. Alternatively, it may be manufactured from a material having a refractive index which continuously decreases from the center to the circumference of the lens. The desired value can be attained by the suitable combination of two materials having different refractive indexes, even if the refractive index of the soft swollen casing is lower than optimum. Also, it is understood that properties of the lens will further change with variations of the refractive index, namely the Young modulus, and the hardness of the material. In order to reduce the volume of the inner part of the lens, this inner part may have the form of a small Fresnel lens, the concentric or spiral scratches and the edges of this lens being suitably protected by a hydrogel coating.

The front side of the lens which reaches into the pupil is automatically centered in the pupil in such a way that it has a convex rotation symmetrical shape of a sphere, paraboloid, or hyperboloid. This shape passes to the broadest circumference as a surface with a shape equal to or approaching the shape of the lateral area of a cone. The hinder side leans against the vitreous body or the capsula and has a spherical, planar, a moderately concave or convex shape, or the shape of a lower part of a rotational ellipsoid. Alternatively, the automatic centering may be obtained by the combination of the spherical shape of the lens either with or without a collar. All surface parts coming into contact with eye tissues must be made of a material having a high water content and low modulus.

The lens according to the present invention may be defined as having a shape which results in automatic centering by its front convex surface leaning against the iris or against the edge of the pupil, this surface being overlapped with a hinder side resting on the membrane of the vitreous body or on the capsula of the lens, whereas all of the surface parts of the lens which are in contact with the eye tissues comprise a soft hydrogel containing at least 70%, advantageously at least 90%, water in the equilibrium swollen state at 20° C. The lens may have a harder core inside having a higher refractive index, with there being either an abrupt or a continuous transition between both materials. For example, a continuous transition of the refractive index can be attained by partially swelling a lens produced from polyHEMA with alkaline hydroxide such that the core remains intact and swells only with 40% of water (See Example 1).

An advantage of the lens of the present invention is that the lens does not wound any part of eye and does not need any support, fastening, or centering means. The highly swelling hydrogel remains clean on the surface, lymphocytes or other cells do not deposit on it, and it has no tendency to form calcifications. Moreover, a great advantage is its easy introduction into the eye while in the partially or completely dried state, i.e., when it possesses its smallest volume. In the state of only partial dehydration, the gel is flexible and can be easily deformed in order to facilitate the insertion to an even greater degree. The dry or almost dry lens increases its volume by swelling about ten times or more and thus fills up the given space and locates itself in the eye axis if the insertion is at least approximately correct. The lens is fixed with the iris on the front side and the hinder side in contact with the vitreous body.

A small difference between the specific masses of the lens and chamber liquor can be compensated for by including a drop of oil into the lens edge during polymerization.

The lens implanted in this way does not seal the back part of the iris even when it sits on the iris since its surface is softer than the surface of the iris. This fact enables the circulation of chamber liquor in the same way as in a sound eye.

Since the lens is supported in front and on a large surface at the back, specific pressures on the neighboring tissues are substantially reduced and the danger of pressure necrosis does not occur.

The lens according to the present invention may be inserted into the original capsule of the natural lens, but may also be implanted without the use of this capsula.

The soft material having a low modulus enables a partial accommodation of the eye.

The lens according to the present invention may be produced, for example, by pressing a prefabricate, produced using a non-crosslinked copolymer of 2-hydroxyethyl methacrylate and a small amount of ethylene dimethacrylate, in a mold in the presence of a strongly acid catalyst. Ethylene dimethacrylate, which usually acts as a crosslinking agent, is used in the procedure according to Czechoslovak Pat. No. 141,101 to Chromecek et al., to produce a copolymer that is well soluble, e.g., in methanol, which is at the most branched but not crosslinked. Another method of manufacturing is the common casting of a mixture of 2-hydroxyethyl methacrylate with less than 2% of ethylene dimethacrylate containing less than 39% of water in stable or rotating molds and the subsequent reorganization of the covalent network by heating with alkaline hydroxide. An additional procedure is described in U.S. patent application No. 022,074 and consists of the crosslinking polymerization of a drop of HEMA containing less than 1% of a crosslinking agent in a mold filled with a liquid immiscible with the given monomers under simultaneous pressing of the polymerizing mixture into the final shape.

The reorganization of the covalent network with the simultaneous increase of the swelling capacity of the polymer in water may also be carried out only in the surface layer of the lens in a manner such that the action of the above given reagents (an acid catalyst or alkaline hydroxide) is limited and the reagent does not penetrate into the entire mass of the lens.

The invention is further illustrated in the following examples of performance and in drawings. Generally, FIGS. 1–4 diagrammatically represent, in partial sectional views, various shapes of the intracameral lenses according to the present invention.

FIG. 1 shows a lens which has a front paraboloidal supporting and centering convex part 1 designed for leaning against the iris and a moderately convex hinder supporting part 2 which enables the lens to lean against a large surface area of the back capsula or a membrane of the vitreous body. The hinder supporting part 2 is broadened and forms a retaining ring 3 on the lens edge which secures the lens, thereby preventing the lens from sliding out into the anterior chamber of the eye.

The lens illustrated in FIG. 2, in contrast to the lens in FIG. 1, shows the front supporting and centering convex part 1 having a spherical shape which passes into the shape of the lateral area of a cone.

EXAMPLE 1

Figure 1:
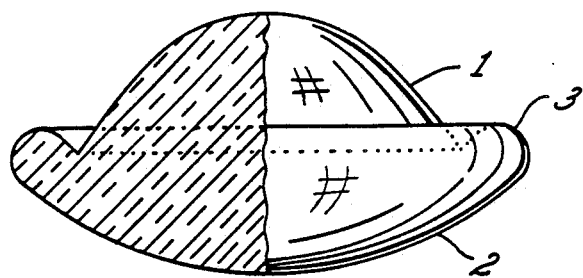
Figure 2:
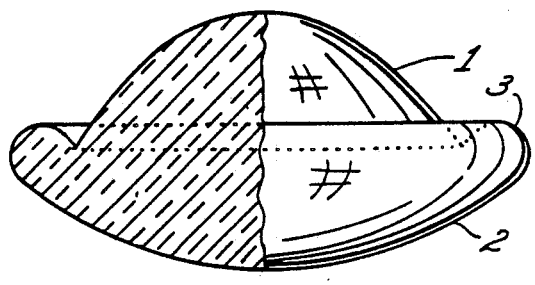
Figure 3:
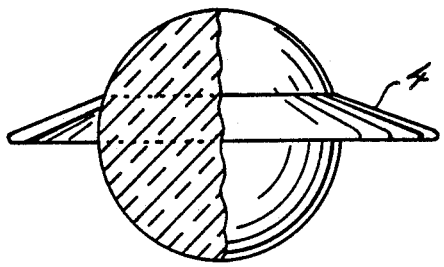
FIG. 3 shows the lens having a spherical shape, the edge of the lens being provided with a soft hydrogel collar 4 which acts in the same manner as the retaining ring 3 of FIG. 1.
Figure 4:
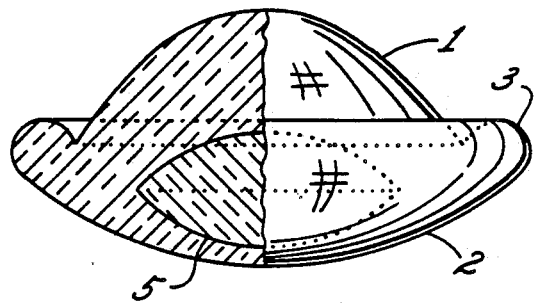
FIG. 4 illustrates the lens according to FIG. 1 which has, inside the optical axis, an inner part 5 which possesses a higher refractive index of light than the hydrogel surrounding this part.

A lens having the shape shown in FIG. 1 was cast in an adequately scaled-down mold with the addition of 0.3% of isopropyl peroxo-carbonate in the presence of 20% of water in monomer mixture. After completion of the polymerization, the lens was washed with distilled water and immersed into 30% sodium hydroxide for 1 hour. The hydroxide was removed from the surface with filter paper, and the lens was heated by infrared radiation above 40° C. in an atmosphere saturated with steam for 16 hours, washed with distilled water, and stored in a 0.8% solution of sodium chloride. The prepared lens increased in volume by about 40% in comparison with the original casting and its surface layer was strongly swollen, the lens containing about 93% water. In the inwards direction, the swelling capacity was 88.5% water at 20° C. in the state of equilibrium swelling.

EXAMPLE 2

The procedure according to Example 1 was repeated with the distinction that the mold was somewhat smaller and the lens was, after washing with water, allowed to stand in the 30% sodium hydroxide for 24 hours at 2° C. and then transferred together with the vessel and hydroxide into a thermostated bath where it was heated to 35° C. for another 24 hours. The lens was then thoroughly washed and had a swelling capacity of 81% water at 20° C. The swelling
in physiological saline at pH 7.1 was 63%. The resulting lens was easily applicable after partial drying and reduction of the volume and did not require centering fixation after reswelling in the eye.

EXAMPLE 3

The required amount of refined paraffin oil and a drop of monomer mixture consisting of 2-hydroxyethyl methacrylate with 0.3% of ethylene glycol dimethacrylate, 35% of water, and 0.1% of azo-bis-isobutyronitrile were introduced into a polypropylene mold having a spherical surface. The mold was closed with a shaped polypropylene punch and heated to 60° C. for 4 hours in a nitrogen atmosphere. The punch was provided on the edge with cuttings which enabled the oil to overflow, the edge of the punch not tightly fitting the mold. The overrun monomer mixture created a rounded border. The mold was then opened and the lens spontaneously fell out. It was rinsed with petroleum, allowed to dry, immersed into a 120° C. warm mixture of from 1 part of sulfuric acid and 3 parts of anhydrous glycerol for 2 minutes, and thoroughly washed with water. It was eventually stored in physiological saline. The resulting lens had a very soft surface layer with such a low friction coefficient that it easily facilitated an automatic centering of the lens in the posterior chamber of eye.

EXAMPLE 4

A small Fresnel lens having fine scratches was polymerized into a viscous polymerizing mixture of 2-hydroxyethyl methacrylate with methacrylic acid producing a swelling copolymer which, after washing and neutralization to pH 7.1, had a water content of 90%. The polymerization was carried out using sodium persulfate and such a slow heating of the mixture as to enable the small Fresnel lens from poly(butyl methacrylate) to be located in the center of a transparent mold while the polymerizing mixture had a considerable viscosity but still before the gelation point, the gelatin point then being rapidly achieved by heating with a source of infrared radiation before the Fresnel lens could change its position. The upper side of the mold was free but was surrounded with an atmosphere of pure nitrogen.

The invention is not limited to the present examples which only illustrate the various possible methods of lens preparation, these methods not being the primary objective of the present invention.

What we claim is:

1. A soft intracameral lens adapted for location in the posterior chamber of an eye wherein said lens has overall spherical shape comprising a front supporting and centering part which, after location of the lens in the posterior chamber of the eye, protrudes anteriorly from the posterior chamber, wherein said front part is adapted for laterally centering said lens in the eye, and a rear supporting part which, after the location of said lens in the posterior chamber of the eye, is adapted for contacting a capsula or a membrane of the eye, and a retaining ring located on said front supporting part comprising an anterior surface, said anterior surface extending radially rearward from the surface of the said front supporting part, wherein the outward extension of the anterior surface of said ring ranges up to about 1.5 mm and the thickness of said lens ranges front about 1 mm to about 3.5 mm, said lens being self-centering and self-supporting after location in the posterior chamber of the eye without the need for additional supporting or centering means, all surface parts of the lens which contact eye tissue being formed from a soft hydrogel which does not wound eye tissue.

* * * * *